(12) United States Patent
Schoene

(10) Patent No.: US 9,566,034 B2
(45) Date of Patent: Feb. 14, 2017

(54) ARRANGEMENT AND METHOD FOR VISUALIZING AN ELECTRICAL SIGNAL

(71) Applicant: Martin Schoene, Berlin (DE)

(72) Inventor: Martin Schoene, Berlin (DE)

(*) Notice: Subject to any disclaimer, the term of this patent is extended or adjusted under 35 U.S.C. 154(b) by 0 days.

(21) Appl. No.: 14/654,609

(22) PCT Filed: Dec. 20, 2012

(86) PCT No.: PCT/EP2012/076381
§ 371 (c)(1),
(2) Date: Jun. 22, 2015

(87) PCT Pub. No.: WO2014/094856
PCT Pub. Date: Jun. 26, 2014

(65) Prior Publication Data
US 2015/0313554 A1   Nov. 5, 2015

(51) Int. Cl.
*A61B 5/00* (2006.01)
*F16M 11/04* (2006.01)
*H02K 33/00* (2006.01)
*G08B 5/22* (2006.01)
*A61B 5/0476* (2006.01)

(52) U.S. Cl.
CPC .......... *A61B 5/7445* (2013.01); *A61B 5/0476* (2013.01); *F16M 11/043* (2013.01); *G08B 5/22* (2013.01); *H02K 33/00* (2013.01)

(58) Field of Classification Search
CPC ... A61B 5/7445; A61B 5/0476; F16M 11/043; H02K 33/00; G08B 5/22
See application file for complete search history.

(56) References Cited

U.S. PATENT DOCUMENTS

| | | | |
|---|---|---|---|
| 3,407,897 A | 10/1968 | Jenny | |
| 2006/0283311 A1* | 12/2006 | Hosler | G10H 3/146 84/723 |
| 2008/0287822 A1 | 11/2008 | Schone | |
| 2009/0141904 A1* | 6/2009 | Reid | G09B 23/14 381/58 |

FOREIGN PATENT DOCUMENTS

| | | |
|---|---|---|
| WO | 2006013311 A1 | 2/2006 |
| WO | 2007045898 A1 | 4/2007 |
| WO | 2007080168 A2 | 7/2007 |

OTHER PUBLICATIONS

Hendrik Rasehorn; "Schwingungen in der Petrischale", Internet Citation, Aug. 17, 2004 (Aug. 17, 2004), XP002455178, Retrieved from the Internet: URL:http://realitaet.hbk-bs.de/new/pdf/bz_artikel.pdf?FUIComponentClass=%5Btype+Function%5D&FScrollBarClass=%5Btype+Function%5D&myXML=(retrieved on Oct. 15, 2007) the whole document—Engl. Abstract.
"Oscillation vs. Vibration" Internet Citation, Dec. 18, 2012, http://vspages.com/oscillation-vs-vibration-4341.

* cited by examiner

*Primary Examiner* — Curtis Odom
(74) *Attorney, Agent, or Firm* — Laurence A. Greenberg; Werner H. Stemer; Ralph E. Locher

(57) ABSTRACT

A method and a configuration for visualizing an electrical signal are provided with a stand, a movable part, an electromechanical actuator and a vessel. The movable part is movable by the electromechanical actuator in at least one stroke direction. The movable part is mechanically connected to the vessel.

9 Claims, 5 Drawing Sheets

ARRANGEMENT AND METHOD FOR VISUALIZING AN ELECTRICAL SIGNAL

BACKGROUND OF THE INVENTION

Field of the Invention

Figure 1:
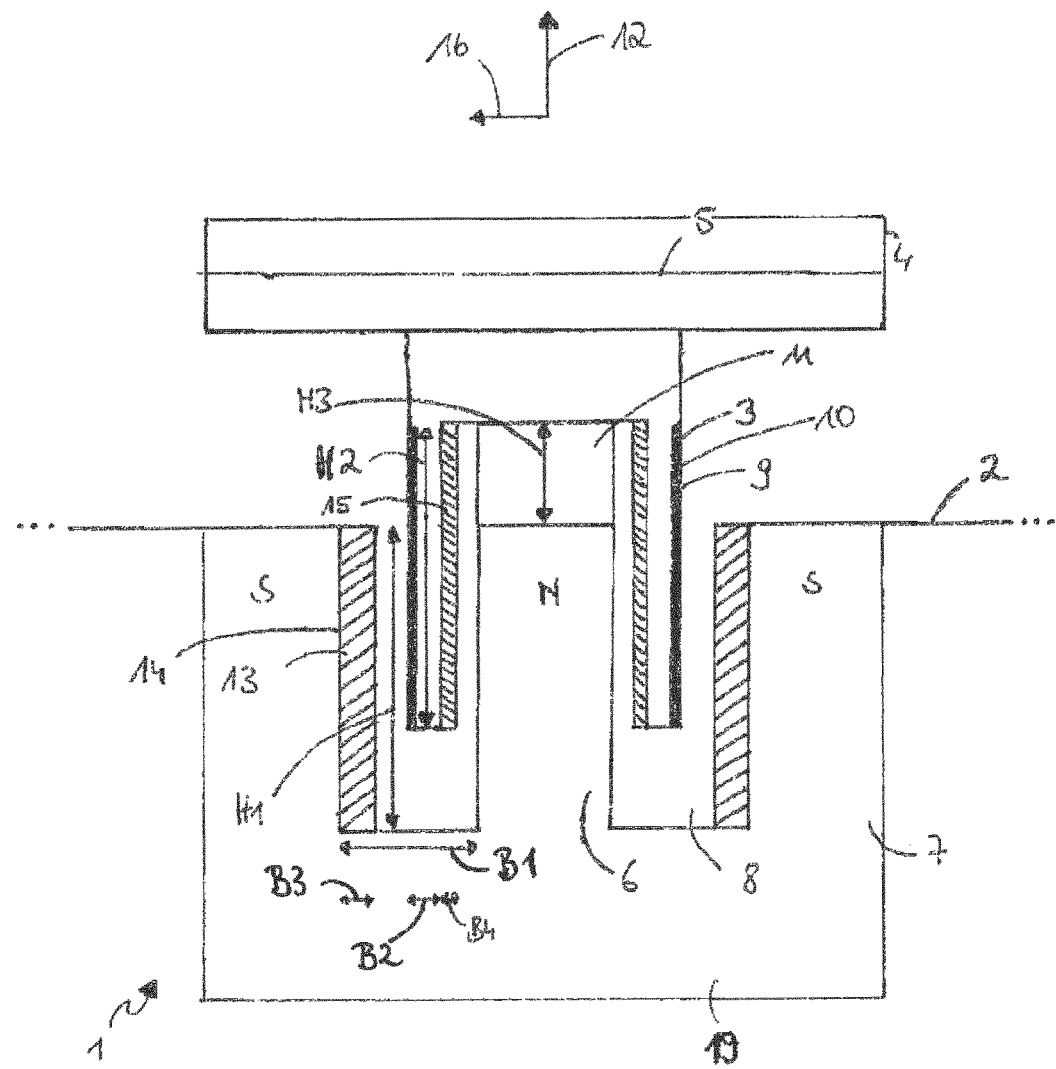

The invention relates to an arrangement and a method for visualizing an electrical signal, in particular a biological signal, such as an EEG signal. An arrangement of the generic kind is known, for example, from WO 2007/080168 A2. The document describes an apparatus for the representation of brain activity through visual patterns. The apparatus comprises a signal-to-frequency modulator, which receives a signal that corresponds to brain activity, and generates an audio signal, which corresponds to the received signal. The apparatus also comprises a resonance chamber, which generates a visual pattern that corresponds to the audio signal. The disclosed apparatus may comprise, e.g., a dish filled with water, which is placed on the resonance chamber. Additionally, the resonance chamber contains a loudspeaker with a diaphragm, which is attached to a magnet. This magnet induces a vibration of the diaphragm. This movement or vibration of the diaphragm is transmitted through a layer of air, present between the diaphragm and the water-filled dish. The so transmitted sound waves cause the dish to vibrate, thereby forming a wave pattern in the water.

The transmission of sound waves through the air, causing the dish to vibrate may in this case lead to a distortion of the signals and produce interfering noises.

BRIEF SUMMARY OF THE INVENTION

The technical problem therefore arises, how to provide an arrangement and a method for visualizing electrical signals, which allow the visualization of the most undistorted electrical signal, at the same time reducing interfering noises produced during the visualization.

The solution for the technical problem is given by the subjects with the characteristics recited below. Further advantageous embodiments of the invention result from the dependent claims.

An arrangement, in particular an arrangement for the visualization of an electrical signal, is suggested. The electrical signal can be a biological signal, preferably an EEG signal. An EEG signal refers to an electric signal with frequency components mainly in the range of 0 to 50 Hz. However, electrical signals with frequencies up to or above 1000 Hz can also be visualized. The arrangement contains a stand and a movable part. Additionally, the arrangement may include a holding device, which serves to hold at least one illuminating device and one image capturing device. The movable part can be moved relative to the stand. The stand is preferably stationary, i.e. mounted in a fixed position. In particular, the stand can be made of a sound-absorbing material. In particular, the stand can be made at least partly from stone or granite. The stand, for example, can be a stone or granite plate.

Moreover, the arrangement comprises an electromechanical actuator and a vessel. The movable part can be moved by the electromechanical actuator in at least one stroke direction. Therefore, the movable part can perform at least one stroke motion. This way, the movable part can be moved in and against the stroke direction. Additionally, as will be explained latter, the movable part can perform vibration movements.

Furthermore, the arrangement may include a guiding device, wherein the guiding device at least guides the stroke motion of the movable part. However, the guiding device can also allow a movement transverse to the direction of movement of the stroke motion (stroke direction). The guiding device, for example, can be designed in such a way, that any amplitude of the movement transverse to the direction of movement of the stroke motion and/or the maximum traveled distance during this movement is smaller than a predetermined threshold value, in particular smaller than the maximum distance traveled during the stroke motion. As a result, the guiding device guides the movable part in the direction of movement of the stroke motion, but at the same time allows a movement play in a direction other than the direction of movement of the stroke motion. This way, a too close guidance of the movement can be avoided, in order to allow the movable part to vibrate in all lateral directions. The stroke motion can, for example, be a linear movement. In this case, the arrangement may include at least one means for linear guidance, which enable the lowest-friction guidance possible of the movable part with a straight-line motion.

Preferably, a guiding device for the movable part is provided, which allows the above-explained vibration. However, it is also possible that the guiding device guides the movement of the movable part without allowing the previously explained vibration.

According to the invention, the movable part is mechanically connected to the vessel. The movable part and the vessel can be, for example, bolted, welded, glued or otherwise mechanically directly connected. In particular, the movable part and the vessel are joined together in such a way, that a movement of the movable part is simultaneously a movement of the vessel. The vessel and the movable part are therefore mechanically coupled. As a result, no transfer medium, such as air, exists between the movable part and the vessel, wherein said transfer medium transmits, for example, sound waves, which are generated by the movable part, to the vessel.

The vessel can, for example, be a dish, a bowl or a cup. The vessel can also be made from transparent, e.g. translucent, material. The vessel can also be an open vessel. In the vessel, an oscillatory or a vibratory, particularly liquid, material can be placed. The oscillatory material can, for example, be water. The oscillatory material can also exhibit the same or similar resonance characteristics as water. The oscillatory material is placed in the vessel in such a way, that a movement of the vessel, in particular an oscillation movement, transfers to the material. This transfer can generate waves in the material or cause the material to produce wave movements or patterns, whose frequency and/or amplitude corresponds to a frequency and/or amplitude of the movement of the vessel, and therefore to a frequency and/or amplitude of movement of the movable part. The vessel is preferably not completely and therefore only partially filled with the oscillatory material. This shall ensure that the material cannot escape from the vessel or spill even during oscillations.

The vessel may include elements for level indication, e.g. markings or engravings. This way, a desired filling level for filling can be displayed in an advantageous way.

The invention advantageously allows the visualization of electrical signals via wave patterns observed in an oscillatory material present in the vessel, which, due to the direct mechanical coupling of the vessel and the movable part, reduces the distortion of the visualization of the electrical signal, and at the same time the interfering noises caused when transmitting oscillations through air.

The arrangement can also be referred to as Neuroresograph.

In another embodiment, the stand comprises or provides a guide groove or guide slot. The stand can, for example, form a guide groove. For example, the guide groove may be arranged in a granite plate stand. If the stand comprises a permanent magnet that is arranged in or on the stand, as will be explained in the following, the permanent magnet can also form the guide groove or the guide groove can be arranged in the permanent magnet. The movable part or a portion of the movable part is movably arranged or arranged to be movable in the guide groove. In this context, the guide groove serves as guide for the movable part. Specifically, the guide groove can guide the previously explained stroke motion of the movable part. The guide groove can therefore be a part of or form the aforementioned guiding device.

For example, the guide groove may be a circular-shaped or annular guide groove. In this case, the stand can have a central pin and an outer part, wherein the circular guide groove is arranged between the central pin and the outer part. In this case, the movable part, as will be explained in more detail below, can comprise a hollow cylindrical portion, which is movably positioned in the circular guide groove. Hereby, a width of the guide groove can be adapted to a thickness or width of the portion of the movable part located in the guide groove. For example, the width of the guide groove can be chosen such that the movable part can perform stroke motion in the stroke direction only and a movement in a direction different from the stroke direction is minimized.

Through the realization of a guide groove as guide device for the movable part a mechanically simply designed guide device is obtained in an advantageous way, which further reduces interfering noises because of the incorporation of the groove into the stand. For this purpose, as previously mentioned, the stand in particular can be made of a sound absorbing material.

In a preferred embodiment, a friction-reducing element and/or a friction-reducing coating is/are arranged at least at one side surface of the guide groove and/or at least at one side surface of the movable part.

In this case, the side surfaces of the guide groove and of the movable part indicate the external surfaces of the stand and of the movable part, which are moved in a stroke motion relative to each other. If the guide groove is realized as a circular guide groove, as previously explained, then the guide groove shows two side surfaces, namely an outer peripheral surface of the central pin and an inner external surface of the outer part. If the movable part is designed at least partly as a hollow cylindrical portion, then this hollow cylindrical portion has an outer lateral surface of the hollow cylindrical portion as side surface, and an inner lateral surface of the hollow cylindrical portion as another side surface.

A first friction-reducing element may, for example, also have a hollow cylindrical shape and rest on or be fastened to the inner lateral surface of the outer portion of the stand. Another friction-reducing element may, for example, also have a hollow cylindrical shape and rest on or be fastened to the inner lateral surface of the hollow cylindrical portion of the movable part. Therefore, friction-reducing elements are arranged between the outer lateral surface of the hollow cylindrical portion of the movable part and the inner lateral surface of the outer portion of the stand, as well as between the outer lateral surface of the central pin and the inner lateral surface of the hollow cylindrical portion of the movable part. The hollow cylindrically designed friction-reducing elements can be shaped, for example, as a rectangle or square in a rolled-out condition.

In this case, the friction-reducing elements reduce the coefficients of static and/or sliding friction between the movable part and the stand. In particular, the friction-reducing elements can be made of plastic. As an example, the friction-reducing elements can be made of clear or transparent plastic.

Alternatively or cumulatively, a friction-reducing coating can be placed or applied between the inner lateral surface of the outer portion of the stand and the outer lateral surface of the hollow cylindrical portion of the movable part and/or between the inner lateral surface of the hollow cylindrical portion of the movable part and the outer lateral surface of the central pin. The friction-reducing coating can, for example, be a silicone oil coating. Other materials, which form a lubricating film, can also be used as coating. The friction-reducing coating can, for example, form a lubricating film, which reduces the coefficient of static friction and/or the coefficient of sliding friction between the stand and the movable part.

This way, the friction of the proposed arrangement can be advantageously reduced. This is particularly important since the electromechanical actuator, unlike the arrangement proposed in WO 2007/080168 A2, has to move not only air, but also the vessel filled with oscillatory material. In order to achieve a cost-effective design requiring a small installation space for the electromechanical actuator, the friction between the movable part and the stand is to be minimized as suggested.

According to the previous explanations, a width of the guide groove can be adapted to a width or thickness of the movable part, and a width or thickness of the friction-reducing element/the friction-reducing elements. For example, a width of the guide groove can be chosen in such a way that stroke motion of the movable part is made possible in the guide groove only in or against the stroke direction, in which the friction-reducing elements and/or the friction-reducing coating is arranged.

In another embodiment, a width of the guide groove is chosen in such a way that—in addition to the stroke direction—the movable part can be moved in the direction perpendicular or transverse to the stroke direction. The guiding device, which may comprise the guide groove, is designed in such a way that the movable part can perform not only the stroke motion in or against the stroke direction, but also lateral and/or rotational movements. As an example, the guide groove can have a width which is between 0.2% to 10% greater than a width or thickness of the portion of the movable part arranged in the guide groove. The guide groove can also have a width that is, for example, 0.2% to 10% greater than the sum of a thickness or width of the portion of the movable part arranged in the guide groove and a width or thickness of the friction-reducing elements also arranged in the guide groove.

As as result, a particularly advantageous agreement between a guide of the movable part in the stroke direction and a movement play of the movable part in a different direction than the stroke direction is achieved in a favorable way.

If an EEG signal is, for example, used as input signal for the electromechanical actuator, a main frequency of the stroke motion can correspond to a main frequency of the EEG signal. Through one, via the movement play enabled, free vibration capability of the movable part in directions different from of the stroke direction, additional frequencies of the EEG signal can also be represented or visualized in an advantageous way. These can, e.g., be present in the EEG signal as harmonics or through frequency overlapping. In particular, the previously mentioned movement play enables an oscillation or vibration of the movable part in all spatial directions, which, e.g., is necessary for visualizing an EEG signal with a main spectrum of 0 Hz to 50 Hz, but also other electrical signals with a predetermined spectrum.

An improved visualization of particularly low-frequency electrical signals can therefore be achieved in an advantageous way by matching a stable guide and a free oscillation capability.

In another embodiment, the arrangement comprises a means for stroke shortening, wherein the means for stroke shortening is arranged so that the movable part in an idle position of the movable part is located in a raised position. The idle position of the movable part describes a position occupied by the movable part in the case that no deflection is caused by the electromechanical actuator, e.g., if there is no input signal applied to the electromechanical actuator. If the movable part, as previously explained, provides at least partly a hollow cylindrical portion and is arranged in a circular groove of the stand, the means for stroke reduction can, e.g., be arranged on an upper front surface of the central pin of the stand. In this case, the means for stroke shortening can, e.g., be realized as plastic disc or plastic cylinder. If a height of the circular groove of the stand corresponds to a height of the hollow cylindrical portion of the movable part, then the movable part is already raised due to the height of the means for stroke shortening, e.g., of the plastic disc, in the idle position.

This is particularly advantageous when the electromechanical actuator comprises a coil which is arranged on the hollow cylindrical portion of the movable part. In this case, it can be obtained by the means for stroke shortening in an advantageous way that the coil in the idle position of the movable part is arranged in such a way that the electromechanical actuator in this idle position exhibits an optimum efficiency in terms of power or force generation, thus preventing a delayed start.

As a result, an operating range of the electromechanical actuator can be adjusted in the idle position of the movable part by means of stroke shortening.

In another embodiment, the arrangement comprises at least one damping element, wherein the damping element dampens a movement of the movable element. Using least one damping element, e.g., a maximum possible acceleration of the movable part can be limited during a movement in the stroke direction or during a movement against the stroke direction. This way, it can be prevented in an advantageous manner, that the oscillatory material present in the vessel spills or escapes from the vessel. This is particularly necessary, as the invention provides a direct mechanical coupling between the movable part and the vessel. In particular, the damping element can damp a stop movement. For example in this case, a stop movement denotes a movement of the movable part from a deflected position into the above-explained idle position. Therefore, this way a hard impact of the movable part, e.g., during a movement against the stroke direction can be avoided in an advantageous manner. By preventing a hard impact, a distorting change of the wave pattern can be avoided in an advantageous manner.

If the movable part is at least partly realized as a hollow cylinder or has a hollow cylindrical portion and is mounted on a central pin of the stand, as previously described, then at least one damping element can, e.g., be positioned on the upper front surface the central pin. Here for example, the previously mentioned means of stroke shortening, such as a plastic disc, and at least one damping element can be arranged on the central pin. As an example, the damping element can be a cylindrical-shaped foam element, which is, e.g., arranged above the plastic disc.

It is also possible that the means for stroke shortening is simultaneously designed as a damping element. In this case, the means for stroke shortening can, e.g., be realized as a cylindrical shaped foam element, which is arranged on the central pin and which is not completely compressed in an idle position of the movable part.

The means for stroke shortening and/or at least one damping element can reduce or prevent an impact or collision, a friction force and/or tilting of the movable part with the stand in an advantageous way.

In another embodiment, the electromechanical actuator comprises at least one permanent magnet and at least one coil. The permanent magnet is arranged in the stand. In this case, one pole of the permanent magnet can, e.g., be arranged in the previously described central pin of the stand, while another pole of the permanent magnet is arranged in the outer part of the stand. The coil is connected to the movable part. If the movable part is at least partly realized as a hollow cylinder, then the coil can be arranged on the hollow cylindrical portion. In particular, the coil can be wound around an outer or inner lateral surface of the hollow cylindrical portion.

Furthermore, depending on a mass of the movable part, in particular depending on a mass of the vessel and its oscillatory material located therein, the electromechanical actuator with designed such that the movable part can be moved by the electromechanical actuator at a predetermined frequency of an electrical input signal such that a predetermined wave amplitude of the oscillatory material located in the vessel can be generated. In this case, the predetermined wave amplitude can, e.g., be generated in the case that the electrical input signal exhibits a predetermined amplitude, such as a maximum amplitude. In this context, the movable part has a mass that among other things depends on the mass of the vessel and on the mass of the oscillatory material arranged therein. The elements of the electromechanical actuator, e.g., the permanent magnet and/or the coil, in particular a number of turns of the coil, are to be chosen in such a way that the actuator generates a predetermined force at a predetermined frequency of the electrical input signal. In this context, the resulting force should be generated in such a way that the desired force acts on the movable part after subtraction of the friction force. Additionally, the elements of the electromechanical actuator can also be chosen in such a way that the actuator generates a force at a predetermined frequency of the electrical input signal in such a way that a predetermined frequency-specific minimum stroke of the movable part occurs. The frequency-specific minimum stroke ensures that, for every frequency, at least the stroke, which is necessary for generating the frequency-specific wave pattern, is achieved.

Additionally, the force to be generated can depend on a friction force, in particular a static friction force and/or a sliding friction force, which is generated during a movement between the movable part and the stand. Thus, the force generated by the electromechanical actuator must overcome a weight force of the movable part, as well as a friction force in such a way that the movable part is accelerated such that a predetermined wave amplitude is generated in the oscillatory material located in the vessel. The predetermined wave amplitude is necessary to, e.g., allow a visual assessment by the eye of an observer or a camera. The predetermined wave amplitude is also necessary to generate a frequency-specific wave pattern. As an example, a higher wave amplitude is required for visualizing lower frequencies (e.g. 5 Hz), than for visualizing higher frequencies (e.g. 15 Hz). In this case, it can be assumed that low frequencies have comparatively large wavelengths. As a result, wave patterns of low frequencies are characterized by very high and large space requiring structures. Therefore, for the generation of such a pattern, a higher stroke is necessary than for patterns of higher frequencies.

It is also possible that the actuator is realized depending on a mass of the movable part in such a way that a ratio of a maximum producible force to the mass is constant. As an example, the ratio between the maximum producible force and the mass can be constant for frequencies that are greater than 0 Hz and smaller than 50 Hz.

It is also possible, that the electromechanical actuator, in particular a strength of the permanent magnet and/or a number of turns of the electromechanical actuator, is designed or selected in such a way that a predetermined ratio of a power to the mass of the movable part is reached, wherein the power is required for a predefined deflection of the movable part in a predefined time. This power corresponds to a power, which is necessary to generate the acceleration and stroke required for the desired patterning of neural frequencies in a predetermined time for a given mass of the movable part. In this case, it can, e.g., be assumed that as the weight increases, the power needed to achieve the desired stroke also increases linearly. This is the case, for example, at a constant input voltage. It can be further assumed that a friction between the stand and the movable part can be kept constant for varying dimensions of the movable part and of the stand as well. For this purpose, the stand and the movable part can be designed such that a friction remains constant even when the dimensions vary. As a result, as the weight increases, the required force or power also increases linearly.

The proposed arrangement allows a well comprehensible visualization of the electrical signal in an advantageous way.

In another embodiment, the electromechanical actuator has a linear frequency within a frequency range from 1 Hz to 50 Hz. This means that the electromechanical actuator maintains the same dynamic characteristics in the aforementioned frequency range. In particular, the electromechanical actuator can generate the same power at all frequencies of the aforementioned frequency range, if the signals show the same amplitude at different frequencies. However, the frequency linearity implicates that the stroke, which is adjustable by the electromechanical actuator, becomes smaller with the increasing frequency. Therefore, a larger stroke can be generated at lower frequencies than at the higher frequencies of the above-mentioned frequency range.

Preferably, the electromechanical actuator is designed as a so-called linear voice coil, or voice coil actuator. This provides the desired frequency linearity of the electromechanical actuator in an advantageous way.

In another embodiment, the movable part has a hollow cylindrically shaped portion, wherein the coil of the electromagnetic actuator is arranged on the hollow cylindrically shaped portion. The stand either features a circular groove or includes or forms it. The hollow cylindrical portion of the movable part is at least partly arranged in the circular groove and is movably mounted therein. This results in a particularly simple design of the proposed arrangement in an advantageous way, where the stand acts as sound and oscillation damping device to reduce unwanted noise generated during a movement of the movable part. In an advantageous manner, the oscillation damping property can prevent an undesirable oscillation build-up of the movable part.

Additionally, the arrangement can include a holding device, which holds at least one illuminating device and one image capturing device. Hereby, the holding device can also serve as cover for the vessel, and thus protect against adverse effects of light. In particular, the holding device can comprise a supporting element with a body, which is designed as a cover body, and can, e.g., be arranged to cover the vessel. In this context, the body can be attached to the supporting element. A camera can be arranged inside the body. The supporting element can either fully extend to the base plate or rest on the base plate at certain points only. In addition to accommodating the camera, the body is also responsible for the function of desired illumination and shading the oscillatory material located in the vessel. Therefore, lighting devices can be arranged within the body, which, e.g., can illuminate the oscillatory material with a predetermined light intensity. Preferably, the body exhibits non-transparent body side walls and an opaque cover on a top so that no external punctual light can penetrate into the body's enclosed interior volume. Furthermore, the body, in particular its side walls and the cover, can be made of plastic, e.g. Plexiglas (PMMA polymethylmethacrylate). The body can, e.g. on its bottom side, include a diffuser plate to scatter the light generated by the lighting devices. The lighting device can be a full-spectrum lighting device. A hole can, e.g., be centered in this diffuser plate. Furthermore, the body can include a hollow element, such as a hollow cylindrically shaped element, wherein the hole of the diffuser plate provides a face-sided opening of the hollow element as well. The hollow element, e.g. realized as a tube, intrudes into the interior volume of the body. The inner walls of the hole and of the hollow element can, for example, be lined i black, e.g. be painted. The image capturing device can be arranged in the hollow element. In particular, the hole of the diffusor plate can be realized and arranged such that a desired shadow falls on the vessel. This way it is possible that water located in the vessel can be photographed or filmed from a predefined position, e.g. from above, without blinding light reflections.

Furthermore, a method of visualizing an electrical signal is proposed, wherein the electrical signal is used as input signal for an electromagnetic actuator. Depending on the input signal, the electromagnetic actuator moves a movable part at least in or against one stroke direction. According to the invention, the electromagnetic actuator moves a vessel mechanically connected to the movable part depending on the input signal, wherein an oscillatory material is located in the vessel. Due to the movement of the vessel, which is transferred onto the oscillatory material, the oscillatory material can form wave patterns that allow the visualization of the electrical signal, in particular of an EEG signal. These movements can, e.g., be captured by a camera, wherein an evaluation unit evaluates the captured wave patterns.

This advantageously results in a method, using which an as undistorted and low noise visualization as possible of the electrical signal, in particular of the brain activity frequencies, is possible.

BRIEF DESCRIPTION OF THE SEVERAL
VIEWS OF THE DRAWING

Figure 2:
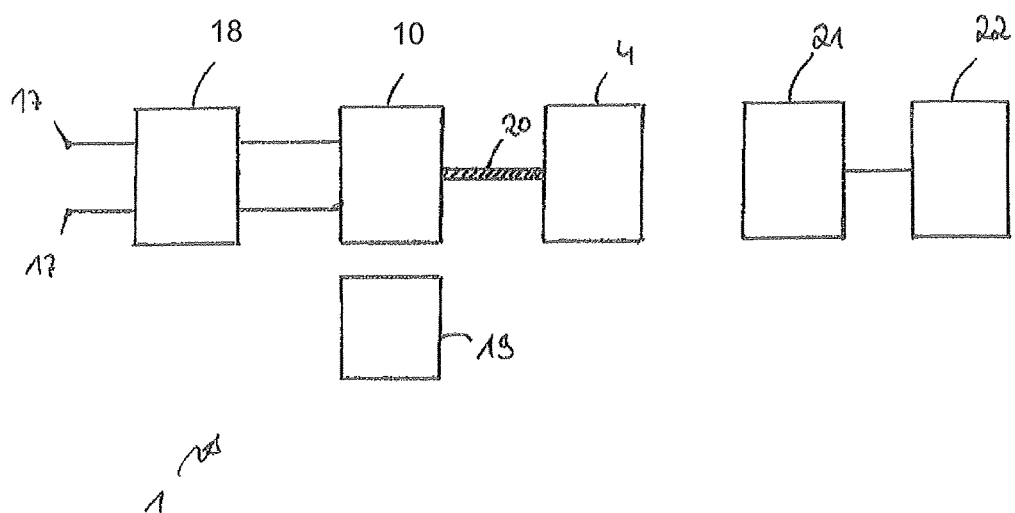
Figure 3:
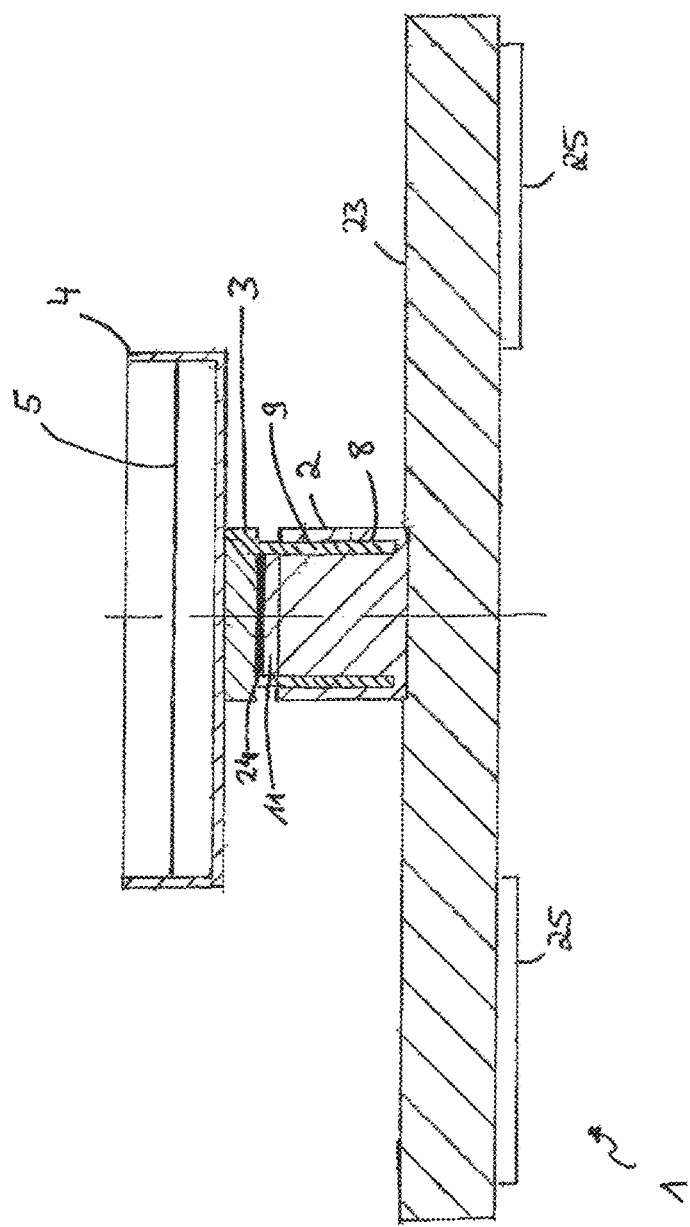
Figure 4:
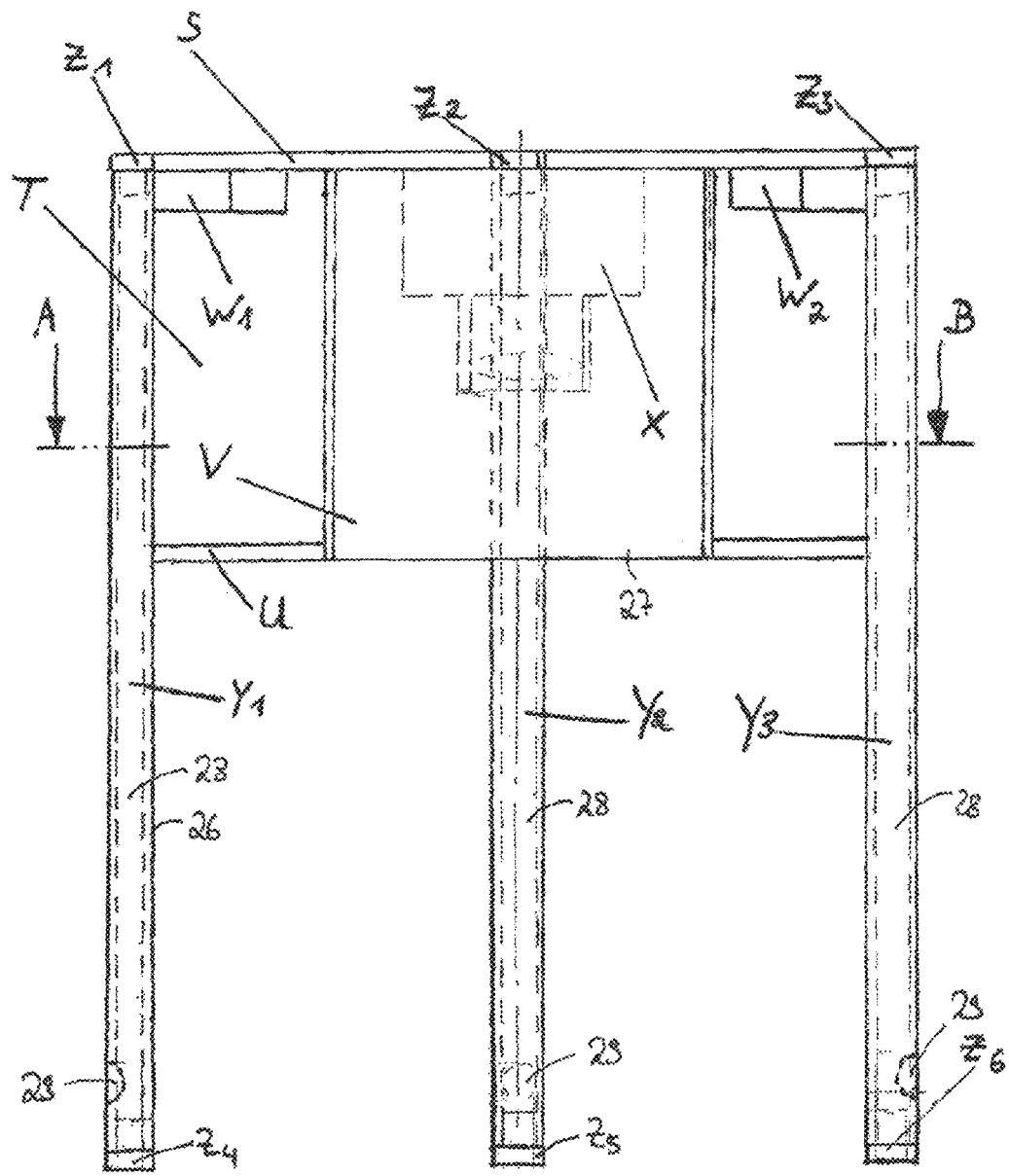
Figure 5:
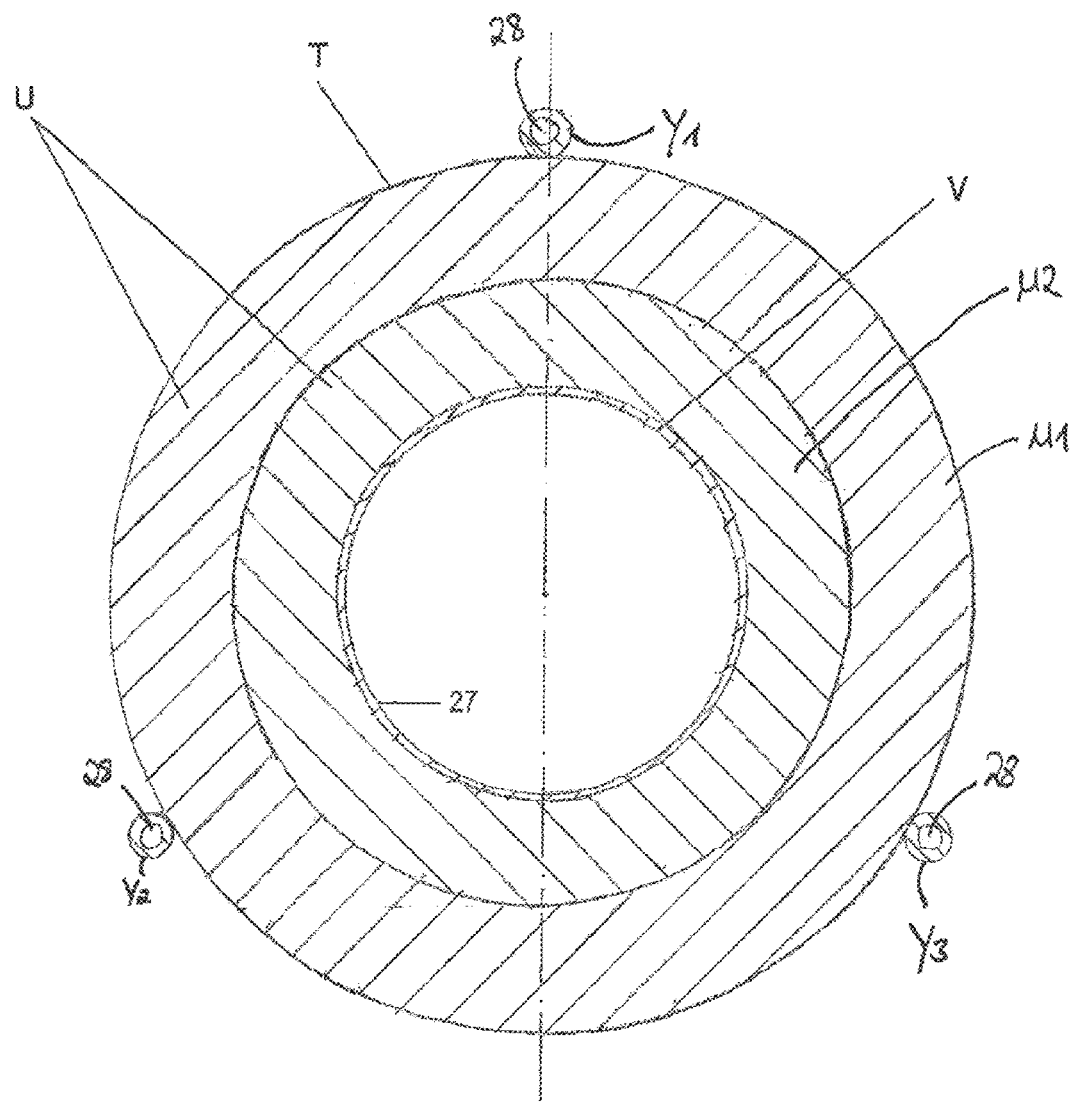

The invention shall be explained in detail based on a design example. The figures show:

FIG. 1 a cross section through an arrangement according to the invention,

FIG. 2 a schematic block diagram of an arrangement according to the invention,

FIG. 3 a cross section through a further arrangement according to the intervention, FIG. 4 an overall view on the supporting element with body, and FIG. 5 a cross section of the supporting element with body

DESCRIPTION OF THE INVENTION

A cross section through an arrangement 1 according to the intervention is shown in FIG. 1. Arrangement 1 comprises a stand 2, which is realized as granite plate. Furthermore, arrangement 1 comprises a movable part 3 and a vessel 4, wherein water 5 is placed in the vessel 4. Vessel 4 is realized as Petri dish with side walls extending perpendicular to a bottom surface. This prevents spilling of water 5 from vessel 4, when movable part 3 is moved. Movable part 3 is firmly mechanically connected with vessel 4. Arrangement 1 further comprises an electromechanical actuator, wherein the electromechanical actuator comprises a permanent magnet 19 (see FIG. 2) having a north pole N and a south pole S. Permanent magnet 19 is arranged in stand 2. Permanent magnet 19 is realized as cylindrical magnet, which is arranged in a cylindrical blind hole in stand 2. In this context, an outer diameter of permanent magnet 19 can correspond to a diameter of the blind hole. This does not exclude the consideration of manufacturing tolerances.

In this context, it is illustrated that permanent magnet 19 realizes or features a central pin 6 and also includes an outer part 7 of permanent magnet 19. A circular or annular groove 8 is arranged between central pin 6 and outer part 7. Movable part 3 comprises a hollow cylindrical portion 9, which is at least partly arranged on central pin 6, wherein at least a part of a wall of the hollow cylindrical portion 9 is arranged in groove 8. In this context, it is shown that groove 8 has a groove height H1. This height H1 is equal to a length or height H2 of hollow cylindrical portion 9. Furthermore, the electromagnetic actuator comprises a coil 10, which is arranged on an outer lateral surface of hollow cylindrical portion 9.

Furthermore, arrangement 1 comprises a cylindrical foam disc 11, which is arranged on central pin 6 and has a height H3. In this context, movable part 3 is shown in an idle position, therefore in a non-deflected position of movable part 3. It is evident that foam disc 11 already raises movable part 3 by height H3 in idle position. As a result, movable part 3 is in a raised position.

The electrical connections of coil 10 are not shown. If a current flows through coil 10, then a force is applied on coil 10 in the magnetic field generated by north pole N and south pole S. This force moves movable part 3, and thus vessel 4 in a stroke direction indicated by arrow 12. Furthermore, a first friction-reducing element 13 is shown, which is realized as a hollow cylinder and which rests against an inner lateral surface 14 of outer part 7 of permanent magnet 19. A second friction-reducing element 15 is also shown, which rests against an inner lateral surface of hollow cylindrical portion 9. First and second friction-reducing elements 13, 15 can, e.g., be made from plastic. First and second friction-reducing elements 13, 15 decrease a static and sliding friction between moving part 3 and permanent magnet 19, which is part of stand 2. Here it is shown that a width B1 of groove 8 is greater than a sum of a wall width B2 of hollow cylindrical portion 9, a wall width B3 of first friction-reducing element 13 and a wall width B4 of second friction-reducing element 15. This results in a horizontal play for movable part 3 in groove 8. This allows a movement of the movable part in a direction which is represented by an arrow 16, perpendicular to the stroke direction (arrow 12). In this case, width B1 is to be chosen in such a way that movable part 3 can still oscillate, however sufficient power transmission is still possible. However, width B1 of groove 8 must not be so large that movable part 3 can tilt or slant, so that water 5, i.e. the oscillatory material, flows out from vessel 4. It is also possible that a width B1 of groove 8 is equal to the sum of wall width B2, wall width B3 of first friction-reducing element 13 and wall width B4 of second friction-reducing element 15.

A camera for recording wave motions of the water 5 as well as a holding device with body in which the camera is arranged, are not shown. These are illustrated in FIG. 4.

A schematic block diagram of an arrangement 1 according to the invention is shown in FIG. 2. Here, connections 17 for an electrical signal, in particular an EEG signal, are shown. An electrical signal to be visualized can be applied to these connections 17. Apparatus 1 comprises an amplifier 18, which amplifies and transmits the applied signal to a coil 10. Coil 10 interacts with a permanent magnet 19, whereby a movement of a vessel 4 is generated. In this context, vessel 4 is mechanically firmly connected to a movable part 3 (see FIG. 1) and hence to coil 10, which is arranged on movable part 3. This is schematically illustrated by a hatched connection 20. Furthermore, arrangement 1 comprises an image capturing device 21, for example, a camera. A data connection can be established between this image capturing device 21 and an evaluation device 22, wherein a wave motion or pattern of water 5 located in vessel 4 can be evaluated by evaluation device 22 via the image recorded by image capturing device 21.

A cross section through another arrangement 1 according to the invention is shown in FIG. 3. Arrangement 1 comprises a stand 2 and a granite plate 23. Stand 2 is arranged on granite plate 23, wherein at least a lower portion of stand 2 is arranged in a form-locking recess, such as a blind hole, of granite plate 23. Furthermore, arrangement 1 comprises a movable part 3 and a vessel 4, wherein water 5 is placed in the vessel 4. Vessel 4 is realized as Petri dish with side walls extending perpendicular to a bottom surface. Movable part 3 is firmly mechanically connected with vessel 4. Arrangement 1 further comprises an electromechanical actuator, wherein the electromechanical actuator comprises a permanent magnet 19 (see FIG. 2) having a north pole N and a south pole S. Here, stand 2 comprises or realizes permanent magnet 19. Furthermore, stand 2 features an annular groove 8. Movable part 3 comprises a hollow cylindrical portion 9, wherein at least a part of a wall of hollow cylindrical portion 9 is arranged in groove 8. Furthermore, the electromagnetic actuator comprises a coil not shown in FIG. 3, which is arranged on an outer lateral surface of hollow cylindrical portion 9.

Furthermore, arrangement 1 comprises a cylindrical foam disc 11 and a cylindrical plastic disc 24, which are arranged concentrically to one another on stand 2 in such a way that when movable part 3 is inserted into stand 2, they are arranged within an inner volume of hollow cylindrical portion 9. In this context, movable part 3 is shown in an idle position, therefore in a non-deflected position of movable part 3. It is evident that foam element 11 and cylindrical plastic disc 24 raise movable part 3 in idle position. As a result, movable part 3 is in a raised position. Plastic disc 24 serves as a means for stroke shortening, while foam disc 11 serves as a damping element.

Furthermore, cylindrically shaped feet 25 of granite plate 23 are shown, which, e.g., can be realized in a rubber granulate, e.g. Ambigran.

FIG. 4 shows an overall view of a holding device, which comprises supporting element 26 and a body T. Supporting element 26 comprises supporting legs $Y_1$, $Y_2$, $Y_3$. Body T comprises diffuser plate U also shown in FIG. 5. Diffuser plate U provides a hole 27 in its center. Hereby, body T is attached to the support legs $Y_1$, $Y_2$, $Y_3$. Hollow cylindrical body T features an upper end plate S and a lower end plate, which is realized as above-mentioned diffuser plate U. Lighting elements $W_1$, $W_2$ are attached to the upper end plate S in an inner volume of the body T. Connection lines for an electrical connection of the lighting elements $W_1$, $W_2$ can be routed through or along one or more supporting legs $Y_1$, $Y_2$, $Y_3$. FIG. 4 illustrates that supporting legs $Y_1$, $Y_2$, $Y_3$ feature ducts 28, e.g., for electrical lines or data lines, which are accessible through holes 29. Damping elements Z1, Z2, Z3, Z4, Z5, Z6 are arranged on both face sides of supporting legs $Y_1$, $Y_2$ and $Y_3$. A tubular element V—whose inner walls are painted black and outer walls are painted silver—is inserted centrally between the end plates S, U. A camera X is positioned in this tubular element V, by means of which a wave pattern of the water 5 in the vessel 4 (see for example FIG. 3) can be imaged. For this purpose, supporting element 26 with body T can be arranged above vessel 4 in such a way that the center axes of camera X, of tubular element V and of hole 27 are aligned with a center axis of vessel 4.

FIG. 5 shows a cross section along the cutting line A-B through supporting element 26 with body T. Diffuser plate U, which comprises two sections U1, U2, is illustrated. An internal section U2 features a blackened surface, while an external section U1 is realized transparent. The blackened surface serves to increase the shadow of tubular element V, which is cast on vessel 4 (see FIG. 3) to prevent reflections. Center hole 27 in the size of tubular element V can also be seen. Tubular element V is connected to diffuser plate V, in particular to internal section U2.

The invention claimed is:

1. A configuration for visualizing an electrical signal, the configuration comprising:
    a stand;
    a vessel;
    an electromechanical actuator including at least one permanent magnet and at least one coil; and
    a movable part mechanically connected to said vessel and movable by said electromechanical actuator at least in one stroke direction;
    said at least one permanent magnet being disposed in said stand;
    said at least one coil being connected to said movable part; and
    depending on a mass of said movable part, said electromechanical actuator being constructed to move said movable part at a predetermined frequency of an electrical input signal for generating a predetermined wave amplitude of an oscillatory material located in said vessel.

2. The configuration according to claim 1, wherein said stand includes or provides a guide groove, and said movable part is movably disposed in said guide groove.

3. The configuration according to claim 2, wherein said guide groove and said movable part have side surfaces, and at least one of a friction-reducing element or a friction-reducing coating is disposed at least on one of said side surfaces.

4. The configuration according to claim 2, wherein said guide groove has a width permitting said movable part to move in a direction perpendicular to said stroke direction in addition to said stroke direction.

5. The configuration according to claim 1, which further comprises a device for stroke shortening, said device for stroke shortening placing said movable part in a raised position in an idle position of said movable part.

6. The configuration according to claim 1, which further comprises at least one damping element for damping a movement of said movable part.

7. The configuration according to claim 1, wherein said electromechanical actuator has a linear frequency in a frequency range of from at least 0 Hz to 50 Hz.

8. The configuration according to claim 1, wherein:
    said movable part has a hollow cylindrical portion;
    said coil is disposed on said hollow cylindrical portion;
    said stand includes or provides a circular groove; and
    said hollow cylindrical portion is at least partly disposed in said circular groove.

9. A method of visualizing an electrical signal, the method comprising the following steps:
    providing a stand;
    providing a vessel;
    providing an oscillatory material in the vessel;
    mechanically connecting a movable part to the vessel;
    providing the electrical signal as an input signal of an electromagnetic actuator including at least one permanent magnet disposed in the stand and at least one coil connected to the movable part; and
    using the electromagnetic actuator to move the movable part and the vessel at least in one stroke direction depending on a predetermined frequency of the input signal and a mass of the movable part for generating a predetermined wave amplitude of the oscillatory material.

* * * * *